(12) United States Patent
Batten et al.

(10) Patent No.: US 9,671,319 B1
(45) Date of Patent: Jun. 6, 2017

(54) SAMPLE PORT

(71) Applicant: Thermaco, Inc., Asheboro, NC (US)

(72) Inventors: William C. Batten, Asheboro, NC (US); Bruce W. Kyles, Asheboro, NC (US)

(73) Assignee: Thermaco, Inc., Asheboro, NC (US)

( * ) Notice: Subject to any disclaimer, the term of this patent is extended or adjusted under 35 U.S.C. 154(b) by 44 days.

(21) Appl. No.: 14/817,905

(22) Filed: Aug. 4, 2015

Related U.S. Application Data

(60) Provisional application No. 62/032,718, filed on Aug. 4, 2014.

(51) Int. Cl.
*G01N 1/20* (2006.01)

(52) U.S. Cl.
CPC ... *G01N 1/2035* (2013.01); *G01N 2001/2071* (2013.01)

(58) Field of Classification Search
CPC . G01N 1/00; G01N 2001/2071; G01N 1/2035
USPC ............................. 73/863.61, 863.86, 864.51
See application file for complete search history.

(56) References Cited

U.S. PATENT DOCUMENTS

| 978,889 | A | 12/1910 | Imhoff | |
|---|---|---|---|---|
| 1,200,951 | A | 10/1916 | Kelly, Jr. | |
| 2,213,458 | A | 9/1940 | Buckley | |
| 2,226,968 | A | 12/1940 | Clerici | |
| 3,224,593 | A | 12/1965 | Nebolsine | |
| 3,719,081 | A * | 3/1973 | Lynn | G01N 1/2035 73/198 |
| 4,372,854 | A | 2/1983 | Szereday | 210/242.3 |
| 4,385,986 | A | 5/1983 | Jaisinghani et al. | 210/123 |
| 4,406,789 | A | 9/1983 | Brignon | 210/519 |
| 4,451,366 | A | 5/1984 | Smisson | 210/209 |
| 4,554,074 | A | 11/1985 | Broughton | 210/519 |
| 4,744,256 | A | 5/1988 | Niskin | 73/864.66 |
| 4,938,878 | A | 7/1990 | Hall | 210/744 |
| 4,985,148 | A | 1/1991 | Monteith | 210/519 |
| 4,986,138 | A | 1/1991 | Spencer | 73/864.34 |
| 5,005,432 | A | 4/1991 | Faulkner | 73/863.86 |
| 5,021,153 | A | 6/1991 | Haws | 210/221.2 |
| 5,172,332 | A | 12/1992 | Hungerford et al. | 364/510 |
| 5,178,754 | A | 1/1993 | Batten et al. | 210/138 |
| 5,225,085 | A | 7/1993 | Napier et al. | 210/705 |
| 5,341,690 | A * | 8/1994 | Dawson | G01N 1/2035 73/863.02 |
| 5,405,538 | A | 4/1995 | Batten | 210/744 |

(Continued)

OTHER PUBLICATIONS

5. Fog Sampling, pp. 18-25 from Considerations for Management of the Discharge of FOG to Sanitary Sewer Systems, undated related technology.

(Continued)

*Primary Examiner* — Michael A Lyons
*Assistant Examiner* — Philip Cotey
(74) *Attorney, Agent, or Firm* — MacCord Mason PLLC (57) ABSTRACT

A fats, oils, and grease waste materials water sampling apparatus includes a housing having an inlet, an outlet, a floor to accommodate a sampling jar below the inlet and an open top. The floor in the housing includes a recessed bottom, the recessed bottom extending between the inlet and the outlet to facilitate receipt of a sample jar for fats, oils, and grease waste materials sampling. Systems and methods for the invention are also described.

21 Claims, 9 Drawing Sheets

(56) References Cited

U.S. PATENT DOCUMENTS

| | | | |
|---|---|---|---|
| 5,413,005 A | 5/1995 | Gray | 73/863.43 |
| 5,453,187 A | 9/1995 | Plumb | 210/202 |
| 5,505,860 A | 4/1996 | Sager | 210/519 |
| 5,560,826 A | 10/1996 | Szereday et al. | 210/522 |
| 5,565,101 A | 10/1996 | Kuntz | 210/304 |
| 5,714,069 A | 2/1998 | Sager | 210/519 |
| 5,718,824 A | 2/1998 | Kannan et al. | 210/207 |
| 5,725,760 A | 3/1998 | Monteith | 210/170 |
| 5,730,872 A | 3/1998 | Rhodes | 210/519 |
| 5,746,911 A | 5/1998 | Pank | 210/170 |
| 5,849,181 A | 12/1998 | Monteith | 210/163 |
| 5,861,098 A | 1/1999 | Morrison | 210/774 |
| 5,974,900 A | 11/1999 | Kalidindi | 73/863.57 |
| 5,993,646 A | 11/1999 | Powers | 210/86 |
| 6,068,765 A | 5/2000 | Monteith | 210/170 |
| 6,238,572 B1 | 5/2001 | Batten | 210/739 |
| 6,413,435 B1 | 7/2002 | Kyles et al. | 210/800 |
| 6,423,548 B1 | 7/2002 | Newberg et al. | 436/174 |
| 6,475,381 B1 | 11/2002 | Gustafsson | 210/151 |
| 6,658,876 B1 * | 12/2003 | Richardson | F25D 17/02 62/201 |
| 6,976,398 B2 | 12/2005 | Leoncavallo et al. | 73/863.52 |
| 7,997,156 B1 | 8/2011 | Batten et al. | 73/863.86 |
| 2001/0027954 A1 * | 10/2001 | Broeders | B01D 17/0205 210/800 |
| 2006/0237362 A1 * | 10/2006 | Weymouth | B01D 21/0012 210/532.1 |
| 2008/0289402 A1 * | 11/2008 | Chowdhury | C02F 1/008 73/61.71 |
| 2012/0222500 A1 * | 9/2012 | Riess | G01N 1/02 73/863.23 |

OTHER PUBLICATIONS

Typical Grease Interceptor & Sample Port Installation from the City of Lubock Water Utilities; undated related technology.

Typical Grease Interceptor Installation; Des Moines Metro Wastewater Reclamation Authority, undated related technology.

Sample Port Detail, Palo Alto Sewer Use Ordinance 16.09.060; Oct. 2000.

* cited by examiner

SAMPLE PORT

This application claims the benefit of U.S. provisional application No. 62/032,718 filed Aug. 4, 2014, of which is incorporated by reference in its entirety.

FIELD OF THE TECHNOLOGY

The present disclosure relates generally to a low cost apparatus and method for evaluating the removal, storage and disposal of fats, oil, grease waste by separation apparatus and, more particularly, to a sample port and sample collector for evaluating the removal of fat, oil, and/or grease from an effluent flow and the passage of grey water to a sewage line.

BACKGROUND

Fat, oil, and grease contaminant removal or recovery systems are well known in the prior art. Over the past thirty years there has been a steady move towards requiring food handling facilities to have systems for servicing kitchen grease-bearing water flows. Sewer system lines can become clogged from the fats, oil and grease waste materials (hereinafter referred to as "F.O.G.") put into the sewer system from food handling facilities. This has led more and more sewer authorities to implement F.O.G. control programs. These programs regulate food handling facilities and the manner in which they process F.O.G. The object of many of these programs is to ensure that food handling facilities remove as much of the fat, oil and grease as possible from the effluent flow, thereby releasing only grey water to the sewer system.

As part of the compliance programs, sewer authorities want to check up on the efficacy of the F.O.G. removal program and compliance with standards. Some localities are mandating that F.O.G. sampling ports be installed downstream of the F.O.G. removal facility, so that the authorities can check to see the quality of the effluent to determine whether it falls within the requirements. In some instances, the sampling ports themselves are actually regulated and must meet particular specifications. Various installations have been known in the prior art, but they are often difficult to access, accumulate excess water retention, present challenges when retrieving samples and have other various undesirable drawbacks.

SUMMARY OF THE INVENTION

In accordance with the present disclosure, sample port devices, collection devices and methods are provided for enabling water samples to be taken to assess F.O.G. levels. In some examples the disclosure provides a housing with an inlet, an outlet, a chamber for the flow of effluent from the inlet to the outlet, and a floor in the housing. The floor includes a recessed bottom. The recessed bottom extends below the inlet to facilitate receipt of a sample jar for F.O.G. sampling. The housing also includes a flume attached to the inlet. The flume may have a smaller diameter than the inlet and extend into the chamber of the housing above the recessed bottom for directing the effluent flow.

In another embodiment of the apparatus a F.O.G. sampling port includes a housing made and configured for installation below ground. The housing includes a top with an opening and an inlet. The inlet is connectable to a flume placed for carrying effluent that may include F.O.G. from the inlet into a chamber in the housing. The inlet leads into the chamber within the housing and connects to the flume. The flume extends into the housing above a housing floor. The floor in the housing includes a recessed bottom and the recessed bottom extends below the inlet to facilitate receipt of a sample jar for F.O.G. sampling within the recessed bottom. The housing has an access path in the top of the housing so that a sampling jar can be lowered through the access path and to the recessed bottom and at the end of the flume to collect effluent that may include F.O.G. passing over the flume and into the sampling jar. Desirably, the housing also has a lid for the housing to cover the access path.

The housing may also include side walls. The side walls may be non-parallel. The side walls may ascend upwardly away from the recessed bottom and toward the open top.

The F.O.G. sampling port may include an extension collar mounted to a top of the housing to extend the access path a variable distance to compensate for variable depths of placement of the housing below ground. In some examples, the inlet and outlet of the housing are generally in line with one another without a significant change in height. In other examples, the inlet and outlet of the housing are off-set.

In a preferred embodiment, the housing and additional parts are made of plastic.

The disclosure is also directed to an adjustable apparatus for enabling water samples to be taken to assess F.O.G. levels including a sampling collector. The sampling collector includes a sampling jar, and adjustable length handle, and a multi-positional connector. The support accepts and secures a F.O.G. sampling jar. An adjustable length handle is able to reach different depths of sampling housing installations. A multi-positional connector adjoins the support and the handle. The connector allows the jar to be positioned and held at various angles during sample collection. A lock may also be included that prohibits angle adjustment during sample collection.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 1A:
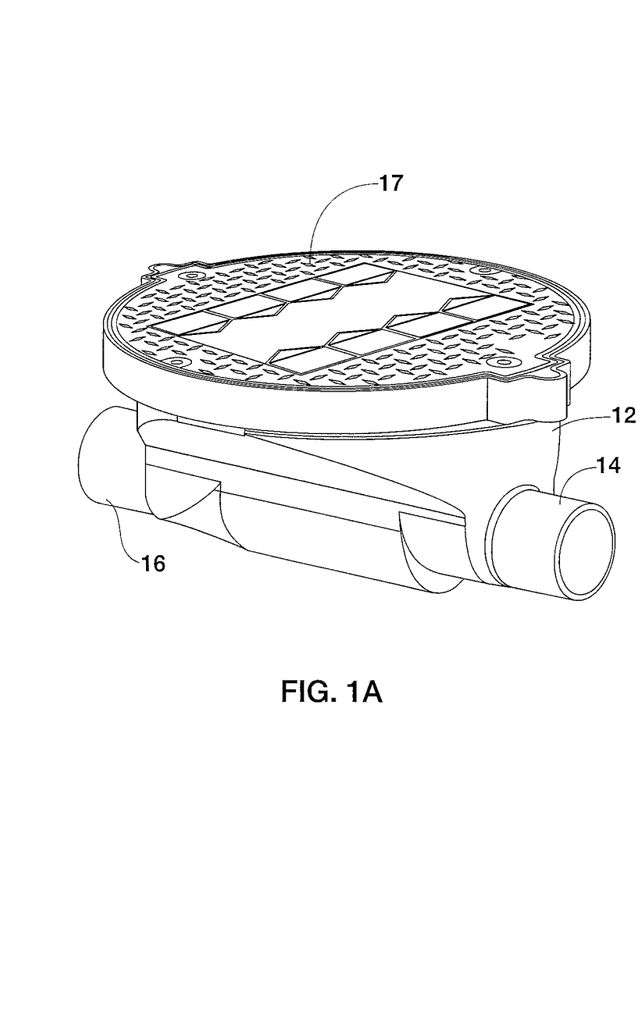
FIGS. 1A-1B are side perspective views of two embodiments of a sample port according to the disclosure.
Figure 1B:
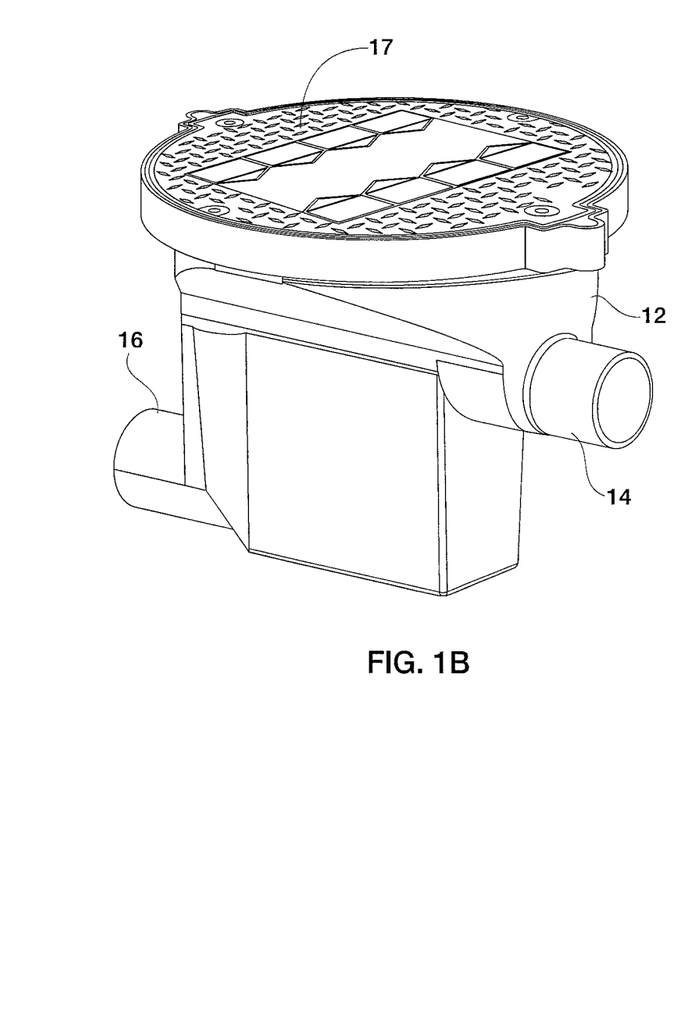

Referring now to the drawings in general and FIG. 1 in particular, it will be understood that the illustrations are for the purpose of describing embodiments of the disclosure and are not intended to limit the disclosure or any invention thereto.

In one embodiment, this disclosure is directed to a system, apparatus and methods for enabling water samples to be taken to assess F.O.G. levels. In one example, as shown in FIGS. 1A and 1B, the apparatus provides a housing 12 that is to be connected to piping that is downstream of a device for removing fats, oils, and grease (F.O.G.) from waste water before it is allowed to pass to a system such as a municipal sewer pipe. The F.O.G. removal device can be any of several types, by way of example, including BIG DIPPER® and TRAPZILLA® products of Thermaco, Inc., Asheboro, N.C., or other point source removal devices or grease traps. The housing 12 has pipe fittings so that it can be connected to upstream and downstream pipe portions to make a continuous path for the effluent. In some cases, the pipe portions may be in line or almost in line with each other, and in other examples, the pipe portions may be offset. The apparatus may be installed as the pipe portions are being installed, such as in new construction, or may be retrofitted to preexisting piping structures.

Applicant's apparatus for enabling water samples is pre-constructed so that it is able to be installed without the need to be assembled and/or constructed on-site, making it easier and quicker to install. As seen in FIG. 1A, the apparatus accommodates in-line pipe portions. Off-set pipe portions are accommodated with the embodiment of FIG. 1B. Features common to both will be referred to herein by the same reference number.

FIGS. 2A-D and FIGS. 3A-E show examples of the apparatus housing 12. The housing 12 includes an inlet 14, an outlet 16, a chamber 21 and an open top 25. A removable lid 17 may be included to cover the open top 25. The inlet 14 and outlet 16 are sized and configured to fit with the upstream and downstream pipe portions to allow for continuous effluent flow. It is desirable for the apparatus to minimize water retention within the chamber 21 and to serve as an effluent flow-through during non-sampling times. The housing 12 is structured to minimize excessive effluent retention.

Since the housing is contemplated to, in some embodiments, be placed below grade, an extension collar (not pictured) may be included and be in communication with housing 12. The one or more extension collars on top of housing 12 increase headspace between the housing top 25 and the lid 17 and/or access port at ground level and the depth of the flume. Since the distance below grade may vary with every installation, the adjustable extension collar can be adjusted to varying heights so it can adapt to the various conditions. Multiple collars may be installed if necessary for additional depth. A removable top cover 17 may be attached to the extension collar provide access for sampling. Extension collars as disclosed in U.S. Pat. No. 7,997,156 to Batten et al. may be used. The entire disclosure of that patent is incorporated herein by reference.

The housing 12 includes a floor 26 and side walls 20 and 22. The floor 26, in some examples, includes a recessed bottom 24. The recessed bottom typically extends below the inlet 14 and toward the outlet 16 to facilitate receipt of a sample jar for F.O.G. sampling. A sloping surface 23 may rise from the recessed bottom 24 toward the outlet 16 to guide the flow of effluent out of the housing 12 through the outlet 16. The side walls 20 and 22 may be non-parallel side walls. In another example, the side walls 20 and 22 may extend upwardly away from the recessed bottom 24 and toward a top 25 of the housing. The walls 20 and 22 may also guide the water flow out of the chamber 21 and discourage water retention within the chamber.

The housing 12 may also include a flume 18. Flume 18 may be attached to the inlet 14. A copper ring, by way of example, may join the flume to the inside of the inlet of the housing 12 using technology described in U.S. Pat. No. 8,002,139, the disclosure of which is incorporated herein by reference. Flume 18 tapers the flow to a smaller diameter than the inlet 14. The flume 18, in one example, may extend into the chamber 21 of the housing above the recessed bottom 24. The smaller diameter flume directs and accelerates the incoming effluent flow from the inlet 14. The flume 18 may include an open top 31 to allow a maximum flow of effluent through the flume without restricting the flow, while still being able to direct and accelerate the effluent flow.

Figure 2A:
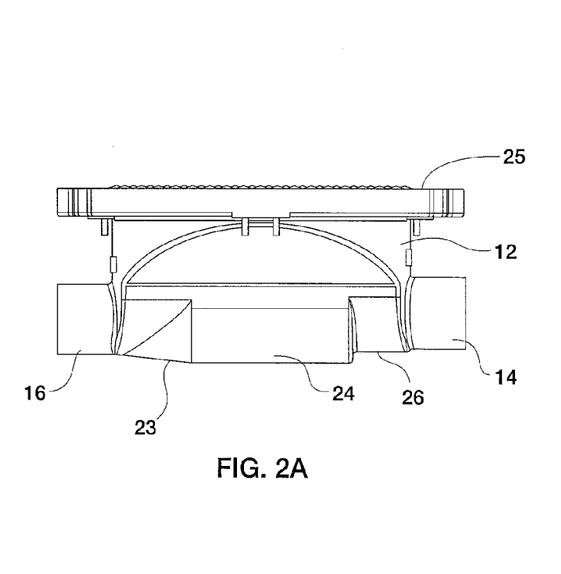
FIG. 2A is a side view of one example of a sample port according to FIG. 1A.
Figure 2B:
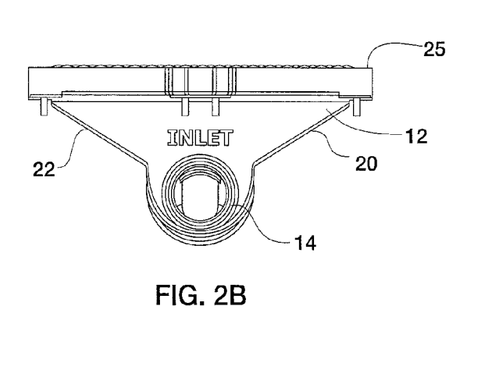
FIG. 2B is an end view of one example of a sample port according to FIG. 1A.
Figure 2C:
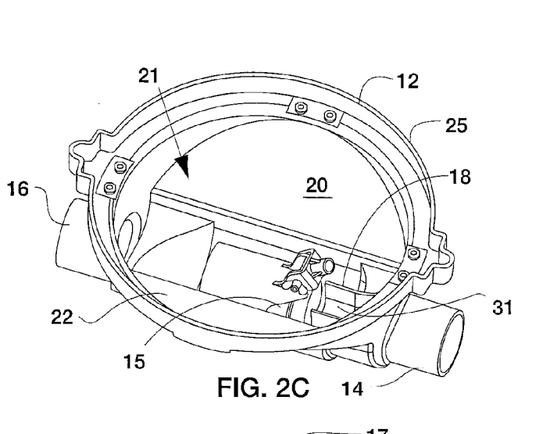
FIG. 2C is a top perspective view into one of the sample ports shown in FIG. 1A with a sample collector within.
Figure 2D:
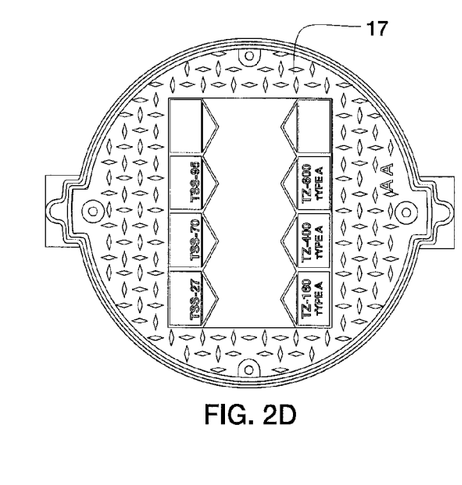
FIG. 2D is a top view of one example of the sample ports shown in FIG. 1A.
Figure 3A:
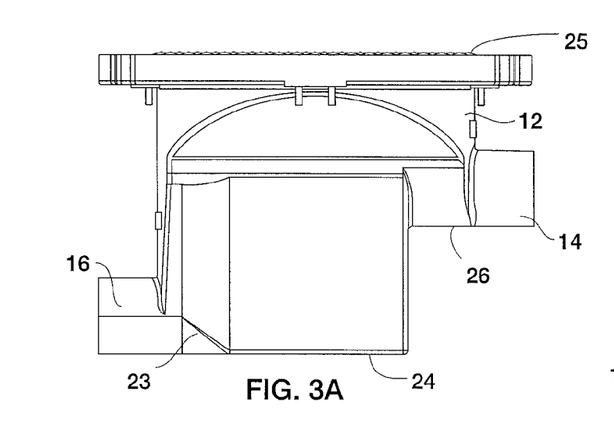
FIG. 3A is a side view of one example of a sample port according to FIG. 1B.
Figure 3B:
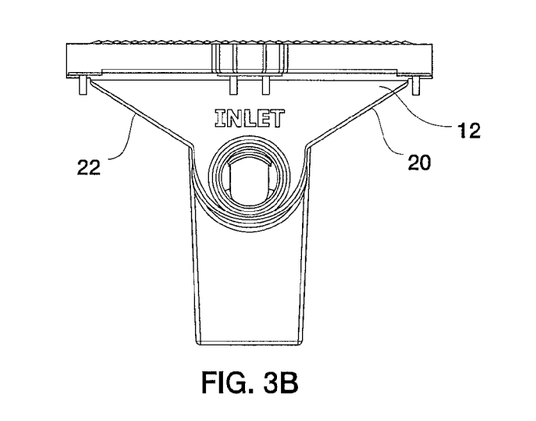
FIG. 3B is an inlet end view of one example of a sample port according to FIG. 1B.
Figure 3C:
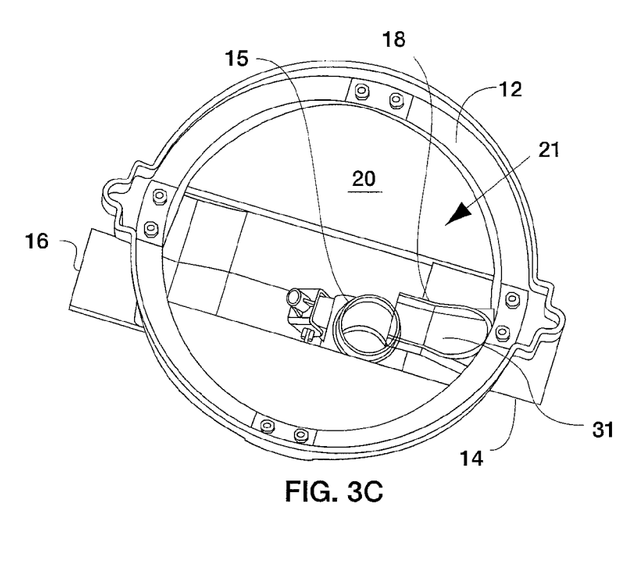
FIG. 3C is a top perspective view into one of the sample ports shown in FIG. 1B.
Figure 3D:
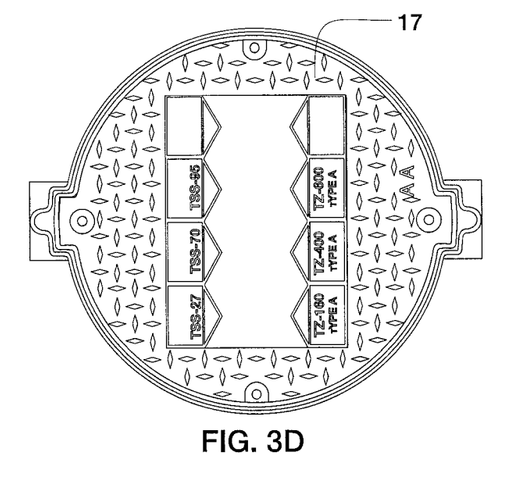
FIG. 3D is a top view of the sample ports shown in FIG. 1B.
Figure 3E:
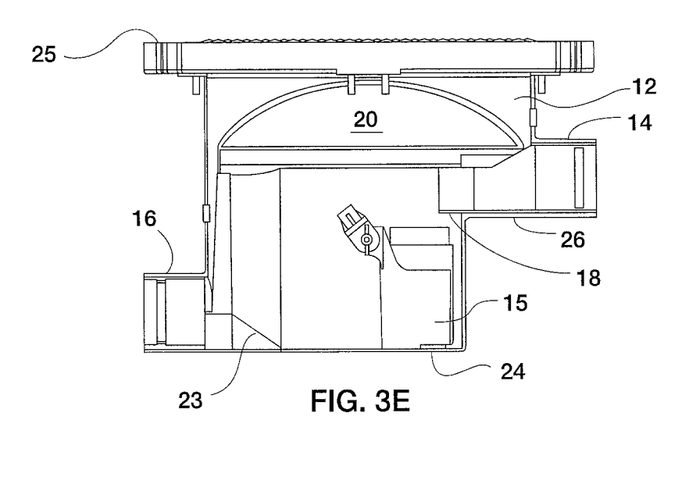
FIG. 3E is a sectional view of one example of the sample ports introduced in FIG. 1B including an example of a sample collector within the sample port.

In some examples, the recessed bottom 24 may include a cylindrical configuration to nest a cylindrical sampling jar 15 in a horizontal position in line with the flume in order to collect an effluent sample (see FIG. 2C). Typically, the apparatus embodiment configured for the in-line pipe portions will allow for horizontal sampling, while the apparatus embodiment for offset pipe portions may better accommodate or be regulated for vertical sampling. Accordingly, in another example, the recessed bottom 24 is spaced below the inlet 14 at a height so that effluent entering the housing through the inlet 14 can fall as a waterfall from the flume 18 to a sample jar 15 placed vertically at a position below the flume 18 during F.O.G. sampling, as seen in FIGS. 3A, C and E.

Figure 4A:
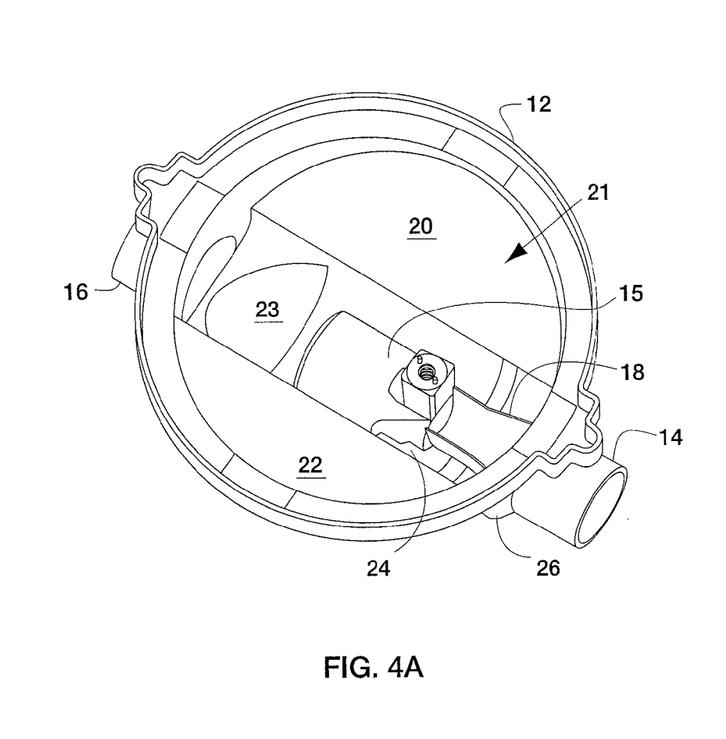
FIGS. 4A-B are top perspective views of embodiments of the invention with the lid removed.
Figure 4B:
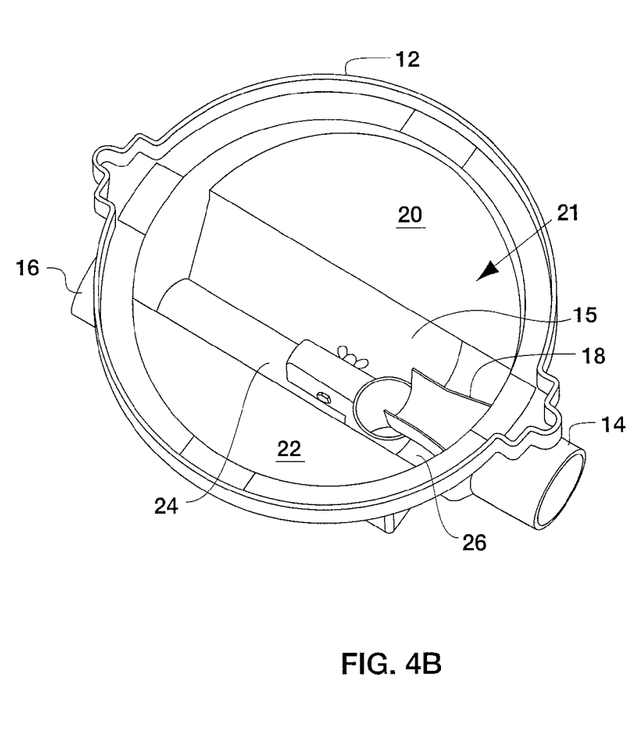
Figure 5:
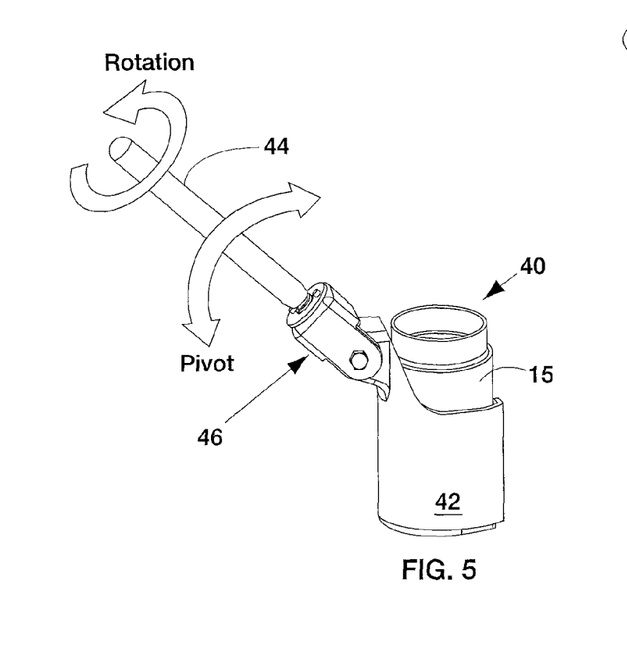
FIG. 5 is a side perspective view of an embodiment of a sample collector.
Figure 6A:
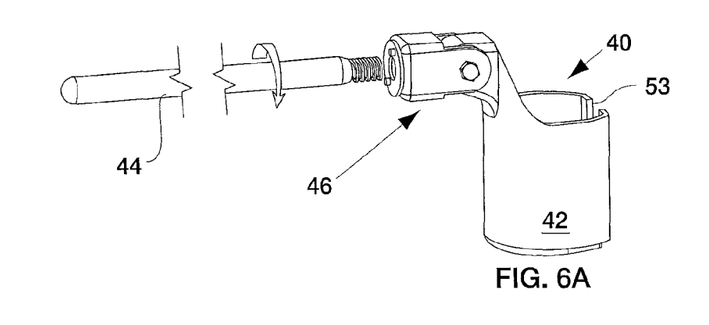
FIG. 6A is a view of the collector with unscrewed handle.
Figure 6B:
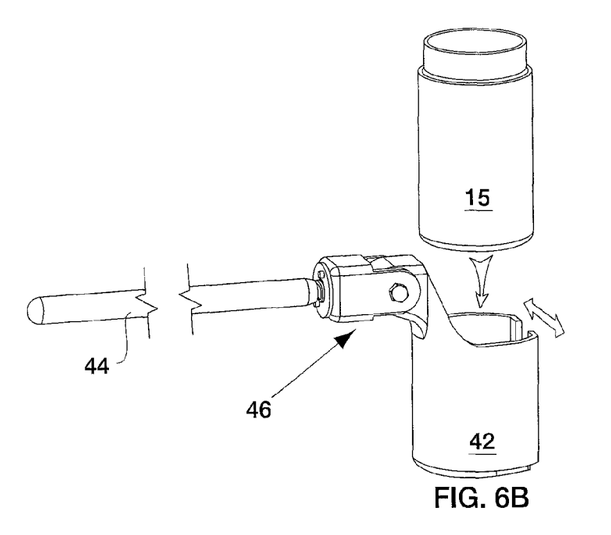
FIG. 6B is an exploded view of the collector of FIG. 5.
Figure 7A:
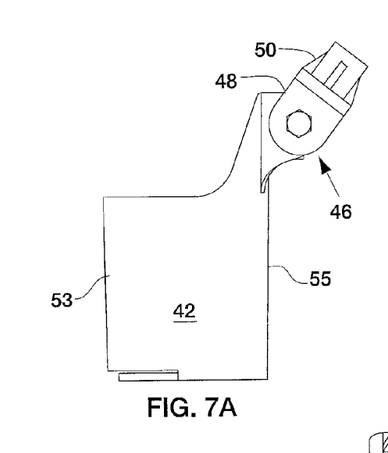
FIG. 7A is a side view of one example of a sample collector according to the disclosure.
Figure 7B:
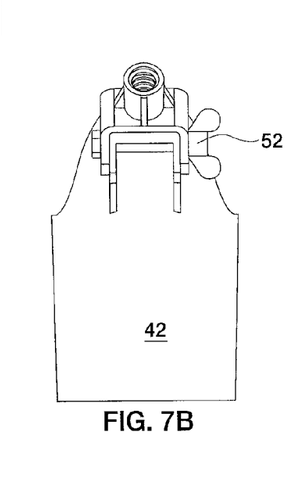
FIG. 7B is a back view of one example of a sample collector according to the disclosure.
Figure 7C:
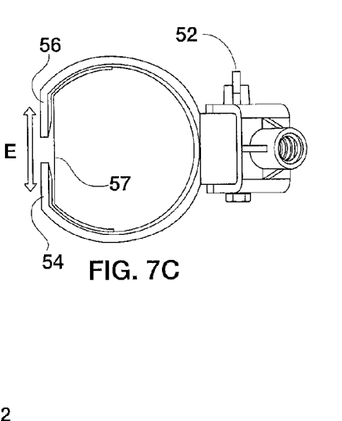
FIG. 7C is a top view of one example of a sample collector according to the disclosure.
Figure 7D:
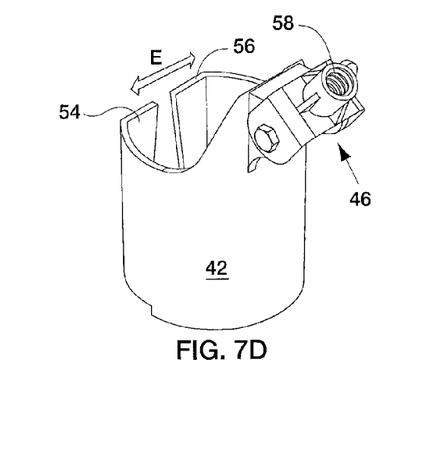
FIG. 7D is a side perspective view of one example of a sample collector according to the disclosure.
Figure 8A:
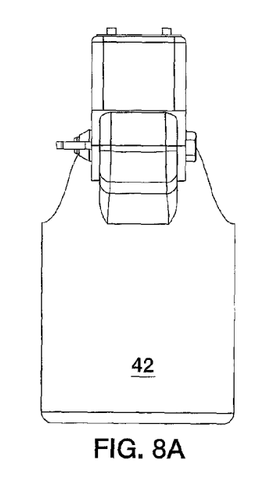
FIG. 8A is a back view of one example of a sample collector according to the disclosure.
Figures 8B, 8C, 8D:
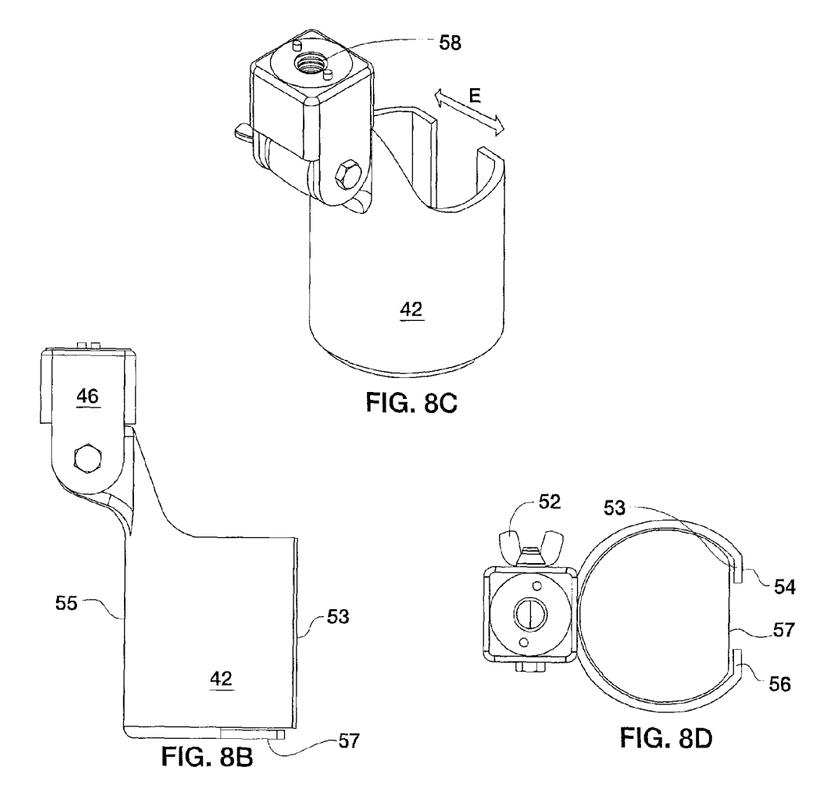
FIG. 8B is a side view of one example of a sample collector according to the disclosure.
FIG. 8C is a side perspective view of one example of a sample collector according to the disclosure.
FIG. 8D is a top view of one example of a sample collector according to the disclosure.
Figure 9:
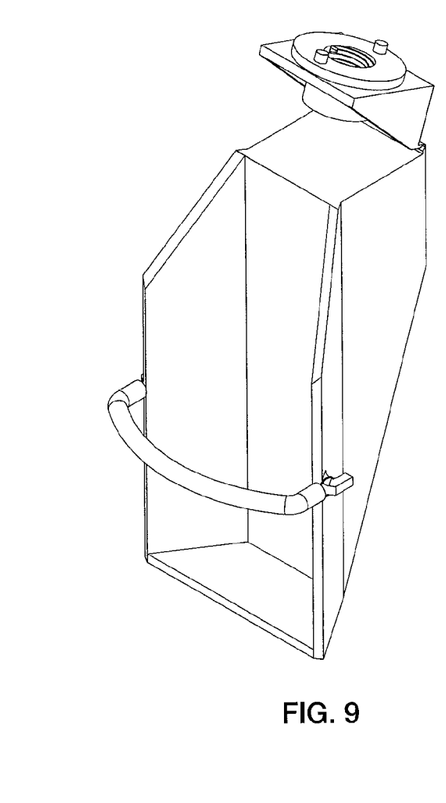
FIG. 9 is another example of a sample collector according to the disclosure.
Figure 10:
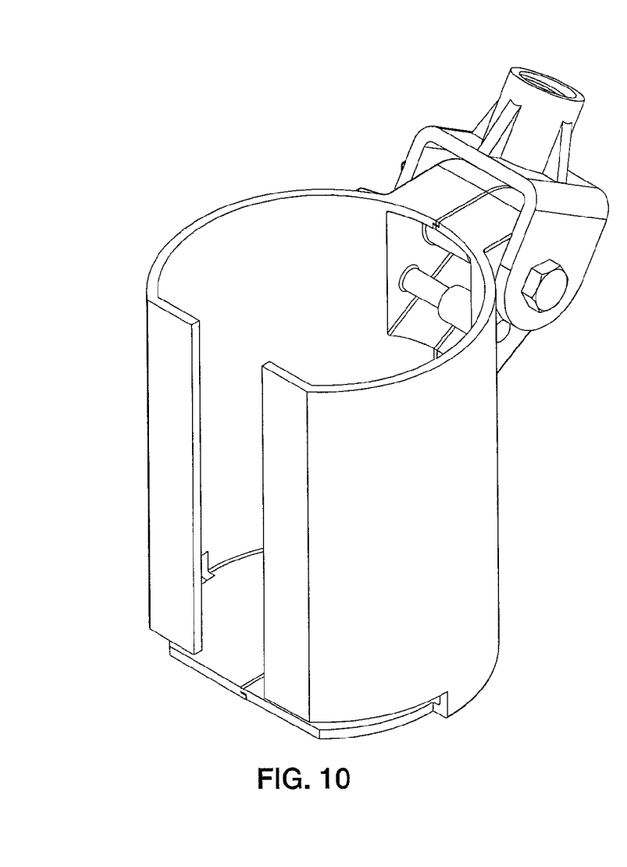
FIG. 10 is another example of a sample collector according to the disclosure.

In another embodiment, as shown in FIGS. 4A and 4B, a F.O.G. sampling port may include a housing 12 made and configured for installation below ground. The apparatus can be installed in a manhole, for example, with a manhole cover. The housing in this example includes a top 25 with an opening and an inlet 14 connected to a flume 18. The flume is placed for carrying effluent that may include F.O.G. from the inlet 14 into a chamber 21 in the housing 12. The inlet 14 leads into the chamber 21 within the housing 12 and connects to the flume 18 above a housing bottom 24. In this example, a recessed bottom 24 in the housing 12 extends downward from floor 26. The floor 26 extends below the inlet 14 to facilitate receipt of a sample jar for F.O.G. sampling within the recessed bottom. The housing includes an access path in the top of the housing 12 so that a sampling jar 15 can be lowered through the access path and to the recessed bottom 24 and at the end of the flume 18 to collect effluent (that may include F.O.G.) passing through the flume 18 and into the sampling jar 15.

In the sampling position, the sampling jar 15 is placed below the inlet of the housing, so that a waterfall effect of the effluent takes place, causing some turbulence of the flow and good mixing of the sample in the sample jar, which some localities require. The recessed bottom 24 and the reduced diameter flume 18 allows the mouth of the sampling jar to nest just under the flume 18 with the jar positioned to receive effluent from the flume in a waterfall motion as the effluent is directed over the flume edge.

When is it desired to take an effluent sample from the apparatus for enabling F.O.G. sampling, the housing 12 is accessed by removing top cover 17 and accessing through open top 25. A sample jar 15 is recessed into the housing 12. Sample jar 15 is positioned at the flume 18. Users may desire to collect two samples, discarding the first sample as a "flush" of the plumbing lines. The variable heights of the apparatus within the ground and angles required for remotely sampling in restricted areas can make obtaining the samples difficult. Accordingly, as shown in FIGS. 5-10, applicant's invention also includes embodiments of an adjustable apparatus 40 for enabling water samples to be taken to assess F.O.G. levels, including a sampling jar support 42, an adjustable length handle 44, and a multi-positional connector 46 for joining the support 42 and the handle 44. The sampling jar support 42 accepts and secures a F.O.G. sampling jar 15. Typically, one liter jars are used for sampling, however, the jar support is preferably configured to accommodate various sampling jar dimensions and sizes.

Often devices used to obtain samples do not secure the sampling jar/collector, making the job of gathering the sample difficult without losing the sample, especially when the jar has to be turned or angled to obtain the sample. In some examples, the support includes a flattened side 53. The flattened side 53 serves to exert a pressure on a circular sampling jar and secures the jar between the inside face of circular side 55 and inside face of flat side 53 of the jar support 42. Forming the support 42 of plastic enables the flexibility of side 53 to grasp the jar within. As seen in FIGS. 7C, 7D, 8C and 8D, the flat side 53 of support 42 may also include a first end 54 and a second end 56, disposed toward each other and expandable away from each other. The expansion between the first end 54 and the second end 56 allows the jar support 42 to extend to accept the sample jar 15 but to hold it securely within the support 42 once placed. Again, making the support 42 of a resilient material facilitates this feature. A support bottom 57 may contribute to cradling the jar in the support.

The adjustable length handle 44 is able to expand to reach different depths of sampling housing apparatus installations. In some examples, the handle 44 is detachable and a longer or shorter handle is attachable as needed. In other examples, the handle itself expands to reach different depths without being removed.

The multi-positional connector 46 joins the support 42 and the handle 44. The connector 46 allows the jar 15 to be positioned and held at various angles during sample collection by the support 42. In one example, seen in FIG. 7, the multi-positional connector 46 may be an injection molded assembly. In another example, seen in FIG. 8, the connector 46 may be a rotationally molded assembly. The handle 44 may be attached to the connector 46: for example, the handle 44 may be threaded into the connector. A rotatable knuckle 50 may allow the handle 44 to rotate in order for a user to adjust the holder in different positions. The connector 46 may further include a hinge 48 that allows the support 42 to be pivoted into different positions.

Once the sampling jar 15 is positioned in the support 42 (FIG. 5), the support 42 securely holds the jar 15 so that the jar stays securely within the support even when the support is tilted to secure a sample. As the depth of the sample port may vary with each sample taken, so also may the angle and requirements at each port for taking the sample. The flexibility of the adjustable apparatus 40 allows the sample to be taken vertically or horizontally and the rotation and hinge movement allows variability of motion while sampling without worrying about the sampling jar slipping. A lock 52 may be included with the apparatus for prohibiting or limiting angle adjustment and/or movement during sample collection. The lock can be as simple as a wingnut on a bolt cinching ears of the hinge together.

Once the sample is collected, the support 42 can be pulled out of the sampling port, the sampling jar 15 can be removed from the support, capped and taken for analysis.

The housing and the associated parts can be made of various materials, for example, of plastic, with molded polyethylene currently preferred.

Systems and methods of the invention are considered within the scope of this disclosure.

Certain modifications and improvements will occur to those skilled in the art upon reading the foregoing description. It should be understood that all such modifications and improvements have been omitted for the sake of conciseness and readability, but are properly within the scope of the following claims.

We claim:

1. An apparatus for enabling water samples to be taken to assess fats, oils, and grease waste materials levels comprising:
   a housing having an inlet, an outlet, and a chamber for the flow of effluent from the inlet to the outlet,
   a floor in the housing having a recessed bottom, the recessed bottom extending between the inlet and the outlet to facilitate receipt of a sample jar for fats, oils, and grease waste materials sampling, and
   a flume attached to the inlet and having a smaller diameter than the inlet to taper and accelerate an effluent flow, the flume extending into the chamber of the housing above the recessed bottom for directing the effluent flow.

2. An apparatus as claimed in claim 1 wherein the flume has a length greater than its diameter.

3. An apparatus as claimed in claim 1 wherein the inlet and outlet of the housing are generally in line with one another and the housing includes side walls that are generally parallel with a line from the inlet to the outlet and that extend away from one another as they extend up from the recessed bottom and toward the top.

4. An apparatus as claimed in claim 3 wherein the floor includes an incline to direct a flow of effluent water from the recessed bottom to the outlet.

5. An apparatus as claimed in claim 1 wherein the inlet and outlet of the housing are generally in line with one another without a significant change in height.

6. An apparatus as claimed in claim 1 wherein the inlet and outlet of the housing are offset so that the outlet is below the inlet.

7. An apparatus as claimed in claim 1 wherein the flume allows a mouth of a sampling jar to nest under the flume so the sampling jar is positioned to receive tapered and accelerated effluent from the flume in a waterfall motion over an edge of the flume.

8. An apparatus as claimed in claim 1 wherein the recessed bottom has a cylindrical configuration to receive a cylindrical sampling jar in a horizontal position in line with the flume in order to collect effluent.

9. An apparatus as claimed in claim 1 wherein the recessed bottom is spaced below the inlet at a height so that tapered and accelerated effluent entering the housing through the inlet can fall as a waterfall from the flume to a sample jar placed in a vertical position below the flume during fats, oils, and grease waste materials sampling.

10. An apparatus as claimed in claim 1 wherein the flume has an open top to allow a maximum flow of effluent through the flume without restricting the effluent flow.

11. An apparatus as claimed in claim 1 further comprising a sample collector including:
    a sampling jar support for accepting and securing a fats, oils, and grease waste materials sampling jar,
    a handle to reach into depths of sampling housing installations,
    a multi-positional connector connecting the support and the handle, the connector allowing the jar to be positioned at various angles during sample collection, and
    a lock for prohibiting angle adjustment during sample collection.

12. An apparatus as claimed in claim 1 wherein the housing has an access path in the top of the housing so that a sampling jar in a sample collector can be lowered through the access path and to the recessed bottom and placed at the end of the flume to collect effluent that may include fats, oils, and grease waste materials passing over the flume and into the sampling jar.

13. An apparatus as claimed in claim 1 further comprising a sample collector including:
    a sampling jar support for accepting and securing a fats, oils, and grease waste materials sampling jar,
    an adjustable length adjustable-length handle to reach different depths of sampling housing installations,
    a multi-positional connector connecting the support and the handle, the connector allowing the jar to be positioned at various angles during sample collection, and
    a lock for prohibiting angle adjustment during sample collection.

14. The apparatus as claimed in claim 11 wherein the sampling jar support includes a flattened side.

15. The apparatus as claimed in claim 14 wherein the flattened side includes a first end and a second end that are able to flex apart from each other to securely accommodate the sampling jar.

16. A fats, oils, and grease waste materials sampling port comprising:
    a housing made and configured for installation below ground,
    the housing having a top with an opening and an inlet for carrying effluent that may include fats, oils, and grease waste materials from the inlet into a chamber in the housing,
    a floor in the housing having a recessed bottom, the recessed bottom extending below the inlet to facilitate receipt of a sample jar for fats, oils, and grease waste materials sampling within the recessed bottom,
    the inlet leading into the chamber within the housing and connecting to a flume that extends into the housing above the housing floor to taper and accelerate effluent from the inlet, and
    wherein the housing has an access path in the top of the housing so that a sampling jar can be lowered through the access path and to the recessed bottom and at the end of the flume to collect effluent that may include fats, oils, and grease waste materials passing over the flume and into the sampling jar.

17. A fats, oils, and grease waste materials sampling port as claimed in claim 16 wherein the inlet and outlet are generally in line with one another and the housing includes side walls that are generally parallel with a line from the inlet to the outlet and that extend away from one another as they extend up from the recessed bottom and toward the top.

18. An adjustable apparatus for enabling water samples to be taken to assess fats, oils, and grease waste materials levels comprising:
    a sampling jar support for accepting and securing a fats, oils, and grease waste materials sampling jar, the sampling jar support being made of a resilient material to hold the sampling jar securely,
    a handle to reach into a depth of a sampling housing installation,
    a multi-positional connector connecting the support and the handle, the connector allowing the jar to be positioned and held at various angles during sample collection, and
    a lock for prohibiting angle adjustment during sample collection.

19. A method of taking water samples to assess fats, oils, and grease waste materials levels comprising:
    opening a housing having an inlet connected to an effluent source, a flume connected to the inlet that tapers and accelerates effluent from the inlet, and an outlet connected to a pipe leading to a sewage treatment plant,
    placing a sampling jar in a recessed bottom of the housing with an open mouth of the sampling jar disposed at the end of the flume to receive tapered and accelerated effluent from the effluent source incoming into the flume and housing through the inlet.

20. A method as claimed in claim 19 including placing a sampling jar in a sampling jar support.

21. A method as claimed in claim 20 including adjusting the angle between the support and a handle to allow the jar to be positioned and held at a particular angle during sample collection.

* * * * *

UNITED STATES PATENT AND TRADEMARK OFFICE
CERTIFICATE OF CORRECTION

| | | |
|---|---|---|
| PATENT NO. | : 9,671,319 B1 | Page 1 of 1 |
| APPLICATION NO. | : 14/817905 | |
| DATED | : June 6, 2017 | |
| INVENTOR(S) | : William C. Batten et al. | |

It is certified that error appears in the above-identified patent and that said Letters Patent is hereby corrected as shown below:

In Column 4, Line 27, after the word --collar--, the words --to provide-- should be inserted.

In Column 5, Line 32, --is it-- should be "it is".

In Column 7, Line 57, the second occurrence of "adjustable-length" should be deleted.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*